United States Patent [19]

Dumont et al.

[11] Patent Number: 4,914,188

[45] Date of Patent: Apr. 3, 1990

[54] NOVEL 6-POSITION CYCLOSPORIN ANALOGS AS NON-IMMUNOSUPPRESSIVE ANTAGONISTS OF CYCLOSPORIN BINDING TO CYCLOPHILIN

[75] Inventors: Francis J. Dumont, Rahway; Philippe L. Durette, New Providence; Arsenio A. Pessolano, Colonia; Joshua S. Boger; Nolan H. Sigal, both of Westfield, all of N.J.

[73] Assignee: Merck & Co., Inc., Rahway, N.J.

[21] Appl. No.: 121,827

[22] Filed: Nov. 16, 1987

[51] Int. Cl.⁴ ............................................... C07K 7/64
[52] U.S. Cl. ...................................... 530/317; 530/321
[58] Field of Search ..................... 530/317, 321, 323; 514/11

[56] References Cited

U.S. PATENT DOCUMENTS

| 4,102,877 | 7/1978 | Nutt | 530/317 |
|---|---|---|---|
| 4,108,985 | 8/1978 | Ruegger et al. | 530/321 |
| 4,117,118 | 9/1978 | Harri et al. | 530/321 |
| 4,210,581 | 7/1980 | Ruegger et al. | 530/321 |
| 4,220,641 | 9/1980 | Traber et al. | 514/11 |
| 4,288,431 | 9/1981 | Traber et al. | 530/321 |
| 4,289,851 | 9/1981 | Traber et al. | 530/321 |
| 4,384,996 | 5/1983 | Bollinger et al. | 530/321 |
| 4,396,542 | 8/1983 | Wenger | 530/321 |
| 4,639,434 | 1/1987 | Wenger et al. | 530/321 |
| 4,681,754 | 7/1987 | Siegl | 514/11 |
| 4,703,033 | 10/1987 | Seebach | 530/321 |

OTHER PUBLICATIONS

R. Wenger, *Total Synthesis—Change in Molecular Structure—Biological Effect: Cyclosporin as Example*, Sandorama, 1984/111, pp. 4–11.

H. Kobel and R. Traber, *Directed Biosynthesis of Cyclosporins*, European J. Appln. Microbiol Biotechnol., 14, 237–240 (1982).

Rudinger, Peptide Hormones, Parsons (ed.), U. Park Press, pp. 1–7 (1976).

*Primary Examiner*—Lester L. Lee
*Assistant Examiner*—Christina Chan
*Attorney, Agent, or Firm*—Joseph F. Diprima; Robert J. North; Curtis C. Panzer

[57] ABSTRACT

Novel cyclosporin analogs containing a MeAla or MeAbu residue at the 6-position of the cyclic undecapeptide have been synthesized and found unexpectedly to exhibit antagonistic activity toward cyclosporin A binding to its cytosolic protein receptor, cyclophilin, without being immunosuppressive.

3 Claims, No Drawings

NOVEL 6-POSITION CYCLOSPORIN ANALOGS AS NON-IMMUNOSUPPRESSIVE ANTAGONISTS OF CYCLOSPORIN BINDING TO CYCLOPHILIN

BACKGROUD OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Crohns disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

The cyclosporins are a family of immunosuppressive compounds isolated from fermentation broths of various fungal species including Tolypocladium inflatum and Cylindrocarpon lucidum.

The generic structure of the class of cyclosporins has been established as a cyclic peptide of formula I which which contains 11 amino acids.

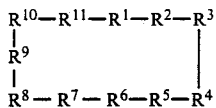

I

For example, cyclosporin A of formula II contains seven N-methylated amino acids and a novel "C-9 amino acid" at position 1, designated as (4R)-4-[(E)-2-butenyl]-4,N-dimethyl-L-threonine(MeBmt). This novel amino acid is located in what is referred to as position 1 and has been found to be important for the immunosuppressive activity of cyclosporin A.

Structure of Cyclosporin A

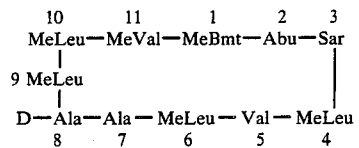

II

Bmt=(4R)-4-[(E)-2-butenyl]-4-methyl-L-threonine
Me=Methyl
Abu=α-Aminobutyric acid
Val=Valine
Ala=Alanine
MeLeu=N-Methyl-leucine
MeVal=N-Methyl-valine
Sar=Sarcosine
Unless specified, the amino acid configuration is L.

Generally, a cyclosporin such as cyclosporin A is not cytotoxic nor myelotoxic. It does not inhibit migration of monocytes nor does it inhibit granulocytes and macrophage action. Its action is specific and leaves most established immune responses intact. However, it is nephrotoxic and is known to cause the following undesirable side effects:
(1) abnormal liver function;
(2) hirsutism;
(3) gum hypertrophy;
(4) tremor;
(5) nephrotoxicity;
(6) hyperasthesia; and
(7) gastrointestinal discomfort.

Cyclosporin A is the only clinically effective immunoregulant on the market today. It is the treatment of choice to prevent rejection of organ transplants. Therapeutic benefits have also been observed in autoimmune diseases, such as type 1 diabetes, multiple sclerosis, uveitis, rheumatoid arthritis, etc. but, in all such cases, broader clinical evaluation and use have been restricted by its severe nephrotoxicity.

The biological activities of cyclosporin A are mediated by an intracellular mechanism, whereby binding to a specific cytosolic protein, called cyclophilin, is responsible for the concentration of cyclosporin A inside the target cells [R. E. Handschumacher et al., Science, 226 (1984) 544]. The specificity of cyclophilin for binding cyclosporin A is indicated by the observation that only those cyclosporin analogs that exhibit immunosuppressive activity in a mixed lymphocyte reaction are capable of binding to cyclophilin. The present invention describes a novel group of cyclosporin analogs that, although not immunosuppressive themselves, are unexpectedly excellent blockers of cyclosporin A binding to cyclophilin. This class of compounds is obtained by substituting the MeLeu residue at the 6-position of cyclosporin A with a MeAla or MeAbu residue. These novel cyclosporin analogs are found to be capable of lowering cyclosporin A-induced nephrotoxicity. Cyclosporin A's desirable immunosuppressive properties, hovever, are not negatively impacted. As evaluated in an in vivo mouse model, the cyclosporin analogs of this invention did not exhibit any nephrotoxicity of their own.

The compounds described in the present invention may also be used to increase the sensitivity of tumor cells that have become resistant to anticancer chemotherapeutic agents, such as vincistine (VCR) and daunorubicin (DNR). Several non-cyclosporin drugs have been shown to exhibit this phenomenon, but clinical application has been limited by toxicity. Cyclosporin A (CsA) has been shown to reverse VCR and DNR resistance [L. Slater et al., *Proc. Am. Assoc. Cancer Res.* 27, 392(1982)], but the associated nephrotoxicity would also restrict its application. This activity of the cyclosporins is dissociable from cyclophilin binding and immunosuppressive activity as evidenced by the observation that a non-immuno-suppressive analog, MeLeu-11-CsA, is as potent as CsA in rendering a tumor cell line sensitive to doxorubicin, as measured by tritiated-thymidine incorporation and cellular proliferation, W. N. Hait et al., *Proc. Am Assoc. Cancer Res.* 28, 298(1987). The compounds described herein are also capable of enhancing the sensitivity of multi-drug resistant cells and, given their lack of nephrotoxicity, as measured in an in vivo mouse model, are expected to find broader clinical application than CSA itself.

Accordingly, an object of the present invention is to provide novel cyclosporin analogs containing a 6-MeAla or 6-MeAbu residue which will interfere with the binding of cyclosporin A to cyclophilin and thereby block the cyclosporin A-induced nephrotoxicity without affecting the immunosuppressive activity of cyclosporin A.

Another object is to provide a novel combination of the cyclosporin analogs of the present invention and cyclosporin A or an active analog thereof for the prevention, control or treatment of immunoregulatory disorders or diseases.

A further object of the present invention is to provide pharmaceutical compositions for administering to a patient undergoing cyclosporin A therapy one or more of the active antagonists of the present invention. The active antagonist(s) can be administered together with, subsequent to or in combination with cyclosporin A or an active analog thereof.

Still a further object of this invention is to provide a method of controlling or suppressing cyclosporin A-induced nephrotoxicity by administering, together with, subsequent to or in combination with cyclosporin A or an active analog thereof, a sufficient amount of one or more of the novel antagonists in a mammalian species undergoing cyclosporin A therapy.

Finally, it is the object of this invention to provide processes for the preparation of the active compounds of the present invention.

DETAILED DESCRIPTION OF THE INVENTION

A. Scope of the Invention

This invention relates to cyclosporins of formula I

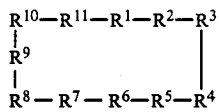     I wherein
$R^1$ is MeBMT or dihydro MeBMT;
$R^2$ is Abu or a fluorinated analog thereof wherein the fluorinated analog represents the amino acid being fluorinated at one or more positions of the side chain, e.g.

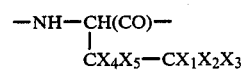     II where $X_1$ to $X_5$ independently are H or F with the proviso that at least one of $X_1$, $X_2$, $X_3$, $X_4$ and $X_5$ is F;
$R^3$ is Sar, D-MeAla or a fluorinated analog thereof;
$R^4$, $R^9$ and $R^{10}$ are independently MeLeu or a fluorinated analog thereof;
$R^5$ is Val or a fluorinated analog thereof;
$R^6$ is MeAla, MeAbu, or a fluorinated analog thereof;
$R^7$ is Ala or a fluorinated derivative thereof;
$R^8$ is (a) D-Ala or a fluorinated derivative thereof; or (b) O-acyl-D-Ser or O-Acyl-D-Thr wherein the acyl group is defined as $R^{12}$—CO— where $R^{12}$ represents hydrogen, $C_{1-6}$alkyl, phenyl or substituted phenyl of formula

wherein $X^1$ and $X^2$ independently are
(a) $C_{1-6}$alkyl especially methyl;
(b) $C_{1-6}$alkanoyl especially acetyl;
(c) $CH_2OH$;
(d) halo especially fluoro or chloro;
(e) $C_{1-6}$alkoxy especially methoxy;
(f) —$NH_2$;
(g) —$NO_2$;
(h) —COOH;
(i) —COO$C_{1-6}$alkyl especially —COOCH$_3$; or
(j) —H; and
$R^{11}$ is MeVal or a fluorinated derivative thereof.

Preferably, this invention relates to cyclosporin analogs of formula I wherein
$R^1$ is MeBmt or dihydro MeBmt;
$R^2$ is Abu;
$R^3$ is Sar or D-MeAla;
$R^4$, $R^9$ and $R^{10}$ independently are MeLeu or a fluorinated analog thereof;
$R^5$ is Val or a fluorinated analog thereof;
$R^6$ is MeAla, MeAbu, or a fluorinated analog thereof;
$R^7$ is Ala;
$R^8$ is D-Ala; and
$R^{11}$ is MeVal or a fluorinated analog thereof.

In an even more preferred embodiment of this invention:
$R^1$ is MeBmt;
$R^2$ is Abu;
$R^3$ is Sar;
$R^4$, $R^9$ and $R^{10}$ are MeLeu;
$R^5$ is Val;
$R^6$ is MeAla;
$R^7$ is Ala;
$R^8$ is D-Ala; and
$R^{11}$ is MeVal;

B. Preparation of the compounds within the scope of the present invention

The 6-position cyclosporin analogs of this invention were prepared via cyclization of appropriate linear undecapeptides following well-established procedures which were slightly modified for better results. The procedure most used is published by R. W. Wenger et al. in *Helv. Chim. Acta*, 67, 502(1984). The following scheme illustrates the application of this procedure to the synthesis of 6-position cyclosporin analogs of this invention:
Starting materials used in the process described in Scheme I are either known or available commercially or are prepared by the following procedures:
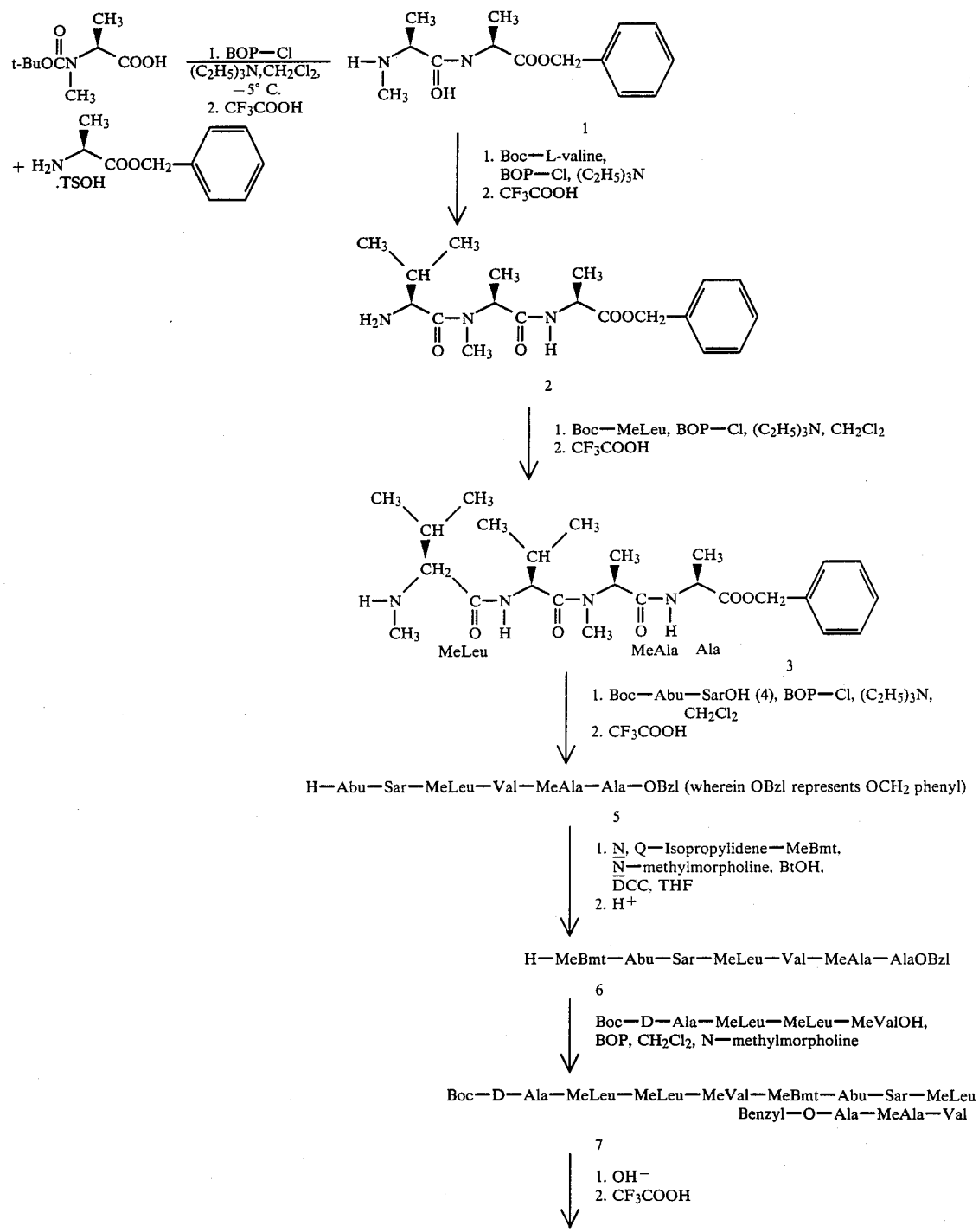

-continued

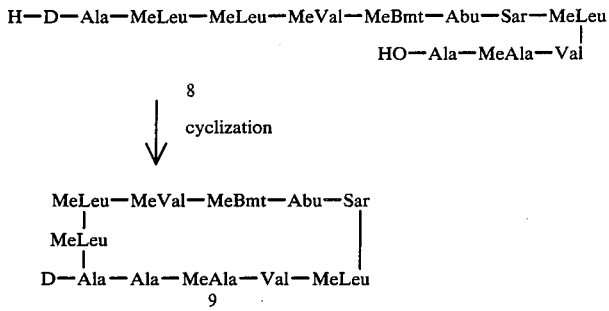

According to the scheme, N-methyl-L-alanine is N-protected as its Boc (t-butyloxycarbonyl) derivative, then coupled with L-alanine benzyl ester p-tosylate salt, in the presence of bis-(2-oxo-3-oxazolidinyl)phosphinic chloride (BOP-Cl) as the peptide coupling reagent, to afford, after removal of the N-protection by trifluoroacetolysis, the O-protected dipeptide 1. Similarly, dipeptide 1 is then coupled with Boc-L-valine, N-deprotected, the derived tripeptide 2 coupled with Boc-MeLeu and N-deprotected to give partially protected tetrapeptide 3. Tetrapeptide 3 is then coupled with the known dipeptide Boc-Abu-Sar-OH (4) [R. M. Wenger, *Helv. Chim. Acta* 67 (1984) 502] with BOP-Cl as the coupling reagent to afford, after N-deprotection with trifluoroacetic acid, the hexapeptide 5.

Heptapeptide 6 is then formed by first coupling with N, O-isopropylidene-MeBMT in the presence of N-hydroxybenzotriazole and 1,3-dicyclohexylcarbodiimide, and subsequent removal of the isopropylidene acetal group by treatment with an acid, for example, HCl in methanol. The protected linear undecapeptide 7 is prepared by condensation of 6 with the known Boc-D-Ala-MeLeu-MeLeu-MeValOH tetrapeptide [R. M. Wenger, *Helv. Chim. Acta* 66 (1983) 2672] in the presence of benzotriazol-1-yloxytris(dimethylamino)phosphonium hexafluorophosphate (BOP reagent). O-deprotection is achieved by treatment with aqueous NaOH in ethanol and N-deprotection by treatment with trifluoroacetic acid. The linear unprotected undecapeptide 8 is then cyclized at high dilution in the presence of a peptide coupling reagent, such as 1-propanephosphonic acid cyclic anhydride in the presence of 4-dimethylaminopyridine, to afford MeAla$^6$-cyclosporin A (9).

The dihydro MeBmt derivatives of the cyclosporin analogs of the present invention are prepared by hydrogenation in an alcohol, such as methanol or ethanol, in the presence of a catalyst, such as, 10% palladium-on-charcoal.

C. Utility of the compounds within the scope of the invention

This invention relates to a method of treating immunoregulatory disorders or diseases. It also relates to a method of treatment for lowering the deleterious nephrotoxic side effects induced by cyclosporin A in patients suffering from immunoregulatory abnormalities and undergoing cyclosporin A therapy. Both mehtods involves (1) the administration of a compound of formula I as the active constituent together with or subsequent to the administration of cyclosporin A or an analog thereof of (2) the administration of a combination of a compound of formula I and cyclosporin A or an active analog thereof.

For lowering the nephrotoxicity of cyclosporin A without affecting the immunosuppressive activity of cyclosporin A, a compound of formula I, either by itself or in combination with cyclosporin A, may be administered orally, topically, or parenterally in dosage unit formulations containing conventional non-toxic pharmaceutically acceptable carriers, adjuvants and vehicles. The term parenteral as used herein includes subcutaneous injections, intravenous, intramuscular, intrastrernal injection or infusion techniques.

The pharmaceutical compositions containing the active ingredient(s) may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay intestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be
(1) suspending agents such as sodium carboxymethylcellulose, methylcellulose, hydroxypropylmethylcellulose, sodium algenate, polyvinylpyrrolidone, gum tragacanth and gum acacia;

(2) dispersing or wetting agents which may be
  (a) a naturally-occurring phosphatide such as lecithin,
  (b) a condensation product of an alkylene oxide with a fatty acid, for example, polyoxyethylene stearate,
  (c) a condensation product of ethylene oxide with a long chain aliphatic alcohol, for example, heptadecaethyleneoxycetanol,
  (d) a condensation product of ethylene oxide with a partial ester derived from a fatty acid and a hexitol such as polyoxyethylene sorbitol monooleate, or
  (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid. Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occuring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in s non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the immunoregulants are employed.

The amount of active ingredient that may be combined with the carrier materials to produce a single dosage form will vary depending upon the host treated and the particular mode of administration. For example, a formulation intended for the oral administration of humans may contain 5 mg to 1 g of an active compound with an appropriate and convenient amount of carrier material which may vary from about 5 to about 95 percent of the total composition. Dosage unit forms will generally contain between from about 25 to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

D. Biological evidence in support of utility of the compounds within the scope of the invention It has been found that the compounds of formula I bind to cyclosporin A's (CsA's) receptor protein, cyclophilin but do not express immunosuppressive activities themselves. They are therefore useful in controlling or lowering the nephrotoxicity induced by cyclosporin A or other active cyclosporin analogs.

The following table illustrates and supports the utility of the compounds of the present invention. Structural specificity can be noted from the data given in the Table in that, of the five 6-position analogs evaluated, only MeAla$^6$-CsA provides a break in the previously established correlation between cyclophilin binding and immunosuppressive activity. Thus, MeAla$^6$-CsA shows 50% of CsA's potency in binding to cyclophilin, but is not immunosuppressive as measured in a T-cell proliferation assay.

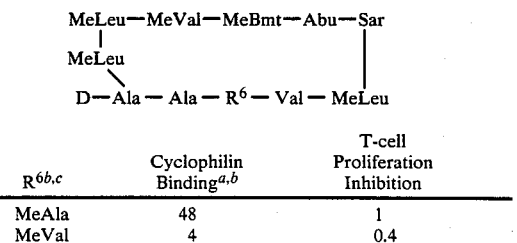

Biological Properties of 6-Position Cyclosporin Analogs

MeLeu—MeVal—MeBmt—Abu—Sar
|
MeLeu
 \
D—Ala — Ala — R$^6$ — Val — MeLeu

| R$^{6b,c}$ | Cyclophilin Binding$^{a,b}$ | T-cell Proliferation Inhibition |
|---|---|---|
| MeAla | 48 | 1 |
| MeVal | 4 | 0.4 |

-continued
Biological Properties of 6-Position
Cyclosporin Analogs

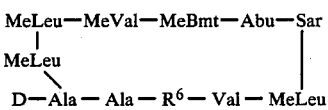

| R[6b,c] | Cyclophilin Binding[a,b] | T-cell Proliferation Inhibition |
|---|---|---|
| MePhe | 16 | 13 |
| MeLeu | 5 | 1 |
| MeNva | 84 | 55 |

[a]This assay is described in detail by R. Handschumacher et al., Science, 226 (1984) 544.
[b]The data are expressed as % CsA's activity (CsA(cyclosporin A) = 100).
[c]T-Cell Proliferation Assay:

T-cell proliferation was measured in mouse T-cell cultures stimulated with ionomycin plus phorbol myristate acetate (PMA). Spleen cell suspensions from C57B1/6 mice were prepared and separated on nylon wool columns. The recovered T-cell were suspended at $10^6$ cells/ml in complete culture medium with addition of ionmycin (250 ng/ml) and PMA (10 ng/ml). The cell suspension was immediately distributed in 96 well-flat bottom microculture plates at 100 $\mu$l/well. Control medium or various concentrations of test compound were added in triplicate wells at 10 $\mu$l/well. The plates were incubated at 37° C. in a humidified atmosphere of 5% $CO_2$-95% air for 44 hours. At 44 hours of culture, the plates received 20 $\mu$l/well of a solution of (3-(4,5-dimethylthiazol-2-yl)-2,5-diphenyltetrazolium bromide (MMT) in PBS (10 mg/ml). To dissolve the purple crystals of MTT formazan produced by metabolically active cells, 100 $\mu$l of a 10% SDS-0.01N hydrochloric acid solution was added to each well. The culture plates were incubated at 37° C. in a 5% $CO_2$ incubator. The plates were read at 570–600 nm a multiwell scanning spectrophotometer. The adsorbance (specific OD) of experimental wells was corrected for that of wells with unstimulated cells or no cells. The percent inhibition of proliferation was calculated according to the formula:

$$\% \text{ Inhib.} = 100 - \frac{\text{Specific OD experimental}}{\text{Specific OD control medium}} \times 100$$

The following example illustrates the processes for making an active compound to be used in the present invention.

Cyclo[-((2S,3R,4R,6E)-3-hydroxy-4-methyl-2-methylamino-6-octenoyl)-L-2-aminobutyryl-sarcosyl-N-methyl-L-leucyl-valyl-N-methyl-L-leucyla-L-alanyl-D-alanyl-N-methyl-L-leucyl-N-methyl-L-leucyl-N-methyl-L-valyl]

Step 1: Boc-N-Methyl-L-Alanyl-L-Alanine benzyl Ester

A stirred solution of 13.41 g (0.066 mole) of Boc-N-methyl-L-alanine and 21.08 g (0.060 mole) of L-alanine benzyl ester tosylate in 350 ml of dry dichloromethane was cooled at −5° C. 32.03 g (0.317 mole) of dry triethylamine was added, followed by 25.0 g (0.099 mole) of N-N-bis(2-oxo-3-oxazolidinyl)phosphinic chloride (BOP-Cl). The reaction was stirred at −5° C. for 24 hours, then washed successively with 125 ml of 10% potassium bisulfate and 2×100 ml of saturated sodium bicarbonate solution. The organic layer was dried over magnesium sulfate and concentrated to a small volume. The crude product was passed through a column of silica gel (Merck #7734) using 1:1 ether/hexane as the eluent, giving 17.1 g (78% of theory) of the blocked dipeptide. Fast Atom Bombardment mass spectroscopy (FAB m.s.) showed a molecular ion peak at 365.

Step 2: N-Methyl-L-Alanyl-L-Alanine benzyl Ester

To a stirred solution of 17 g (0.0466 mole) of Boc-N-methyl-L-alanyl-L-alanine benzyl ester in 150 ml of dry dichloromethane, cooled at −10° C., was added 100 ml trifluoroacetic acid, which was previously cooled at −10° C. The reaction mixture was stirred for 16 hours at −5° C., then poured carefully with good stirring into a mixture of 177 g of sodium bicarbonate, ice, and 150 ml of dichloromethane. The organic layer was separated and the aqueous layer was further extracted with another 60 ml of dichloromethane. The combined organic layers were washed with 3×50 ml of saturated sodium bicarbonate solution, dried over manesium sulfate, and evaporated to give 11.6 g (91% of theory) of crude product which was used in step 3 without further purification.

Step 3: Boc-L-Valyl-N-Mehtyl-L-Alanyl-L-Alanine Benzyl Ester

A mixture of 10.75 g (0.0407 mole) of N-methyl-L-alanyl-L-alanine benzyl ester and 9.73 g (0.0448 mole) of Boc-L-valine in 200 ml of dry dichloromethane was stirred and cooled at −10° C. as 9.97 g (0.0986 mole) of triethylamine was added. After stirring for 15 minutes, 12.55 g (0.0493 mole) of BOP-Cl was added and the reaction was stirred at −5° C. for 22 hours. The reaction was diluted with 100 ml of dichloromethane, washed with 100 ml of 10% potassium bisulfate, washed with 2×75 ml of saturated sodium bicarbonate solution, dried over magnesium sulfate, concentrated, and chromatographed on silica gel using 1:1 ether/hexane as the eluent. The product weighed 17.1 g (91% of theory). Its 200 MHz NMR spectrum in chloroform-d was consistent with the proposed structure.

Step 4: L-Valyl-N-Methyl-L-Alanyl-L-Alanine Benzyl Ester

A stirred solution of 17 g (0.0367 mole) Boc-L-valyl-N-methyl-L-alanyl-L-alanine benzyl ester in 170 ml of dry dichloromethane was cooled at −10° C. as 85 ml of trifluoroacetic acid, previously cooled at −15° C., was added. After 16 hours −5° C., the reaction was carefully poured with good stirring into a mixture of 93 g of sodium bicarbonate, ice, and 250 ml of dichloromethane. The organic layer was separated and the aqueous layer was extracted with another 75 ml of dichloromethane. The combined organic layers were washed with 3×75 ml of saturated sodium bicarbonate solution, dried over magnesium sulfate, and evaporated to give 12.8 g (96% of theory) of crude product which was used in step 5 without further purification. FAB m.s. showed a molecular ion peak at 364.

Step 5:
Boc-N-Methyl-L-Leucyl-L-Valyl-N-Methyl-L-Alanyl-L-Alanine Benzyl Ester

A solution of 3.17 g (0.0537 mole) of Boc-N-methyl-L-leucine in 370 ml of dry dichloromethane was stirred and cooled at 0° C. as one-half of 13.15 g. (0.130 mole)

of dry triethylamine was added, followed by 15.05 g (0.0591 mole) of BOP-CCl. This was stirred at 0° C. for 3 hours. The remainder of the triethylamine was added, followed by a solution of 13 g (0.0358 mole) of L-valyl-N-methyl-L-alanyl-L-alanine benzyl ester in 50 ml of dry dichloromethane. The reaction was stirred at ice temperature for 22 hours, then washed with 125 ml of a 10% solution of potassium bisulfate. The organic layer was further washed with 2×100 ml of saturated sodium bicarbonate solution, dried over magnesium sulfate, concentrated to a small volume, and chromatographed on silica gel eluting with 1:1 ether/hexane gradually increasing the ether to 2:1. The product weighed 15.8 g (75% of theory), and the FAB m.s. showed a molecular ion peak at 591.

Step 6:
N-Methyl-L-Leucyl-L-Valyl-N-Methyl-L-Alanyl-L-Alanine Benzyl Ester

A solution of 15.7 g (0.0266 mole) of Boc-N-methyl-L-leucyl-L-valyl-N-methyl-L-alanyl-L-alanine benzyl ester in 125 ml of dry dichloromethane was stirred and cooled to −10° C. while 70 ml trifluoroacetic acid, previously cooled at −15° C., was added. After 2 hours, the reaction was carefully added with good stirring to a mixture of 105 g of sodium bicarbonate, ice, and 200 ml of dichloromethane. The organic layer was separated and the aqueous layer was extracted with another 50 ml of dichloromethane. The combined organic layers were washed with 3×80 ml of saturated sodium bicarbonate solution, dried over magnesium fulfate, and evaporated leaving 11.85 g (91% of theory) of product. The FAB m.s. showed a molecular ion peak at 491.

Step 7:
Boc-L-2-Aminobutyryl-Sarcosyl-N-Methyl-L-Leucyl-L-Valyl-N-Methyl-L-Alanyl-L-Alanine Benzyl Ester A solution of 11.7 g (0.0238 mole) of N-methyl-L-leucyl-L-valyl-N-methyl-L-alanyl-L-alanine benzyl ester and 7.19 g (0.0262 mole) of Boc-L-2-aminobutyryl-sarcosine [R. M. Wenger, Helv. Chim Acta 67 (1984) 502] in 400 ml of dry dichloromethane was stirred and cooled at −10° C., as 6.41 g (0.0634 mole) of dry triethylamine was added, followed by 7.33 g (0.0288 mole) of BOP-Cl. After stirring for 72 hours, the reaction was washed with 3×100 ml of saturated sodium bicarbonate solution. The organic layer was dried over magnesium sulfate, evaporated, and chromatographed on silica gel using 1:1 ether/ethyl acetate as the eluent. The product weighed 9.1 g (51% of theory) and the FAB m.s. showed a molecular ion peak at 747.

Step 8:
L-2-Aminobutyryl-Sarcosyl-N-Methyl-L-Leucyl-L-Valyl-N-Methyl-L-Alanyl-L-Alanine Benzyl Ester A solution of 9.0 g (0.0120 mole) of Boc-L-2-aminobutyryl-sarcosyl-N-methyl-L-leucyl-L-valyl-N-methyl-L-alanyl-L-alanine benzyl ester in 90 ml of dry dichloromethane was stirred and cooled at −10° C. as 60 ml of trifluoroacetic acid, previously cooled at −10° C., was added. After 16 hours, the reaction was carefully poured into a mixture of 90 g of sodium bicarbonate, ice, and 100 ml of dichloromethane. The organic layer was separated and the aqueous layer was extracted with 75 ml of dichloromethane. The combined organic layers were washed with 3×75 ml of saturated sodium bicarbonate solution, dried over magnesium sulfate, and evaporated. The crude product weighed 7.0 g (90% of theory), and was used in step 9 without further purification. The FAB m.s. showed a molecular ion peak at 647.

Step 9:
((4S,5R,1′R,3′E)-2,2,3-Trimethyl-5-(1′-methyl-3′-pentenyl)-4-oxazolidinecarbonyl)-L-2-aminobutyryl-sarcosyl-N-methyl-L-leucyl-L-valyl-N-methyl-L-alanyl-L-alanine benzyl ester To a mixture of (4S,5R,1′R,3′E)-2,2,3-trimethyl-5-(1′-methyl-3′-pentenyl)-4-oxazolidinecarboxylic acid (prepared by heating at reflux temperature a solution of (2S,3R,4R,6E)-3-hydroxy-4-methyl-2-methylamino-6-octenoic acid [prepared by the process set forth in R. M. Wenger, Helv. Chim. Acta, 66 (1983) 2308]. (250 mg., 1.24 mmol.) in dry acetone (80 ml) for 24 hours and subsequent evaporation under diminished pressure) in 1 ml acetone were added, successively with stirring under a nitrogen atmosphere, dry tetrahydrofuran (10 ml), N-methylmorpholine (152 μl, 1.40 mmol.), N-hydroxybenzotriazole (335.7 mg., 2.48 mmol.), and L-2-aminobutyryl-sarcosyl-N-methyl-L-leucyl-valyl-N-methyl-L-alanyl-L-alanine benzyl ester (803 mg., 1.24 mmol.). The reaction mixture was cooled in an ice bath and 1,3-dicyclohexylcarbodiimide (267.8 mg., 1.30 mmol) added. The mixture was allowed to attain room temperature, and stirring was continued for an additional 24 hours. The mixture was diluted with dichloromethane (60 ml) and washed with saturated sodium hydrogencarbonate solution (30 ml). The aqueous layer was extracted with dichloromethane (30 ml), and the combined organic extracts were dried (sodium sulfate) and evaporated. The residue was triturated with diethyl ether, filtered, and evaporated. The resulting crude material was applied to a column of silica gel (Merck #7734, packed as a slurry in 2% methanol in dichloromethane). Elution was effected with 2% methanol in dichloromethane. Fractions containing pure product were combined and evaporated to afford the protected N,O-isopropylidene-MeBmt-Abu-Sar-MeLeu-Val-MeAla-AlaOBzl heptapeptide as a thick syrup; yield 629 mg. (58%). Its 200 MHz NMR spectrum in chloroform-d was in accord with the desired structure.

Step 10:
((2s,3R,4R,6E-)-3-Hydroxy-4-methyl-2-methylamino-6-octenoyl)-L-2-aminobutyryl-sarcosyl-N-methyl-L-leucyl-L-valyl-N-methyl-L-alanyl-L-alanine benzyl ester To a solution of N,O-isopropylidene-MeBmt-Abu-Sar-Meleu-Val-MeAla-Ala-OBzl (620 mg., 0.71 mmol) in methanol (8 ml) was added with stirring 1N hydrochloric acid (0.70 ml). The reaction mixture was stirred for 18 hours at room temperature, then neutralized with solid sodium hydrogencarbonate (410 mg). The mixture was filtered, the filter washed with methanol, and the combined filtrate and washings evaporated. The crude material was taken up in dichloromethane and filtered. The resulting syrup was dissolved in a small volume of dichloromethane, and the solution was applied to a column of silica gel (Merck #7734, packed as a slurry in 4% methanol in dichloromethane). Elution was effected with 4% methanol in dichloromethane. Fractions containing slower-moving product were combined and evaporated to give the partially protected H-MeBmt-Abu-Sar-MeLeu-Val-MeAla-AlaOBzl heptapeptide as a thick syrup; yield 368 mg (61%).

Step 11:
Boc-D-Alanyl-N-methyl-L-leucyl-N-methyl-L-leucyl-N-methyl-L-valyl-(2S,3R,4R,6E-)-3-hydroxy-4-methyl-2-methylamino-6-octenoyl)-L-2-aminobutyryl-sarcosyl-N-methyl-L-leucyl-L-valyl-N-methyl-L-alanyl-L-alanine benzyl ester To a solution of Boc-D-Ala-MeLeu-MeLeu-MeValOH [prepared by the process set forth in R. M. Wenger, *Helv. Chim. Acta*, 66 (1983) 2672] (246 mg, 0.442 mmol) and H-MeBmt-Abu-Sar-MeLeu-Val-MeAla-AlaOBzl (368 mg., 0.443 mmol) in dry dichloromethane (11 ml) were added N-methylmorpholine (48.7 μl, 0.443 mmol) and benzotriazol-1-yloxytris(dimethylamino)phosphonium hexafluorophosphate (196 mg, 0.443 mmol). The reaction mixture was stirred 5 days at room temperature under a nitrogen atmosphere. It was then diluted with dichloromethane (100 ml), washed with water (50 ml), dried (sodium sulfate) and evaporated. The crude product was chromatographed on a column of silica gel (Merck #7734, packed as a slurry in 4% methanol in dichloromethane). Elution was effected with 4% methanol in dichloromethane. Fractions containing pure product were combined and evaporated to give the desired Boc-D-Ala-MeLeu-MeLeu-MeVal-MeBmt-Abu-Sar-MeLeu-Val-MeAla-AlaOBzl undecapeptide; yield 349.8 mg. (57.6%).

Step 12:
Boc-D-Alanyl-N-methyl-L-leucyl-N-methyl-L-leucyl-N-methyl-L-valvyl-((2S,3R,4R,6E-)-3-hydroxy-4-methyl-2-methylamino-6-octenoyl)-L-2-aminobutyryl-sarcosyl-N-methyl-L-leucyl-L-valyl-N-methyl-L-alanyl-L-alanine To a solution Boc-D-Ala-MeLeu-MeLeu-MeVal-MeBmt-Abu-Sar-MeLeu-Val-MeAla-AlaOBzl (330 mg., 0.241 mmol) in ethanol (10 ml) cooled to ice temperature was added 0.2N aqueous sodium hydroxide (1.2 ml). The reaction mixture was kept at 5° C. for 24 hours, brought to pH 5 with several drops of glacial acetic acid and then evaporated under diminished pressure. The residue was taken up in dichloromethane (30 ml) and washed with water (15 ml). The aqueous layer was extracted with dichloromethane (15 ml), and the combined organic extracts were dried (sodium sulfate) and evaporated. The resulting material was applied to a column of silica gel (Merck #7734, packed as a slurry in 4% methanol in dichloromethane). Elution initially with 4% methanol in dichloromethane gave unreacted starting material and benzyl alcohol; subsequent elution with 15% methanol in dichloromethane afforded the partially protected Boc-D-Ala-MeLeu-MeLeu-MeVal-MeBmt-Abu-Sar-MeLeu-Val-MeAla-AlaOH undecapeptide; yield 239 mg. (77.5%).

Step 13:
D-Alanyl-N-methyl-L-leucyl-N-methyl-L-leucyl-N-methyl-L-valyl-((2S,3R,4R,6E-)-3-hydroxy-4-methyl-2-methylamino-6-octenoyl)-L-2-aminobutyryl-sarcosyl--aminobutyryl-sarcosyl-N-methyl-L-leucyl-L-valyl-N-methyl-L-alanyl-L-alanine Boc-D-Ala-MeLeu-MeLeu-MeVal-MeBmt-Abu-Sar-MeLeu-Val-MeAla-AlaOH (239 mg., 0.187 mmol) was cooled to −15° C. and treated with precooled trifluoroacetic acid (3 ml) for 1 hour at −15° C. The reaction mixture was then evaporated under diminished pressure (bath temperature of 0° C.) and coevaporated several times with dichloromethane. The crude material was taken up in dichloromethane (30 ml) and washed with saturated sodium hydrogencarbonate solution (15 ml). The organic layer was dried (sodium sulfate) and evaporated. The product was triturated with diethyl ether and the resulting amorphous solid was filtered, washed with ether and dried in vacuo; yield 195 mg. (88.6%).

Step 14:
(Cyclo[-((2S,3R,4R,6E)-3-Hydroxy-4-methyl-2-methylamino-6-octenoyl)-L-2-aminobutyryl-sarcosyl-N-methyl-L-leucyl-Valyl-N-methyl-L-alanyl-L-alanyl-D-alanyl-N-methyl-L-leucyl-N-methyl-L-leucyl-N-methyl-L-valyl]

To a solution of H-D-Ala-MeLeu-MeLeu-MeVal-MeBmt-Abu-Sar-MeLeu-Val-MeAla-AlaOH (195 mg., 0.165 mmol) in dichloromethane (650 ml) were added 4-dimethylaminopyridine (97 mg., 0.794 mmol) followed by 1-propanephosphonic acid cyclic anhydride (50 wt. % solution in dichloromethane) (0.2 ml). The reaction mixture was stirred at room temperature for 24 hours, concentrated down to 50 ml and washed with saturated sodium hydrogencarbonate solution. The organic layer was dried (sodium sulfate) and evaporated. The crude material was applied to a column of silica gel (Merck #7734, packed as a slurry in 3:1 hexane-acetone). Elution was effected intitially with 3:1 hexane-acetone). Elution was effected initially with 3:1 hexane-acetone and subsequently with 2:1 hexane-acetone. Fractions containing pu-re product were combined and evaporated to give MeAla$^6$-CsA as a white amorphous solid; yield 121 mg. (63%). Its 400 MHz NMR spectrum in chloroform-d was in accord with the desired structure. FAB m.s. showed a molecular ion at m/z 1160.

What is claimed is:

1. A compound of formula

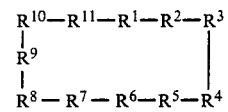

I wherein:

$R^1$ is MeBMT or dihydro MeBMT;

$R^2$ is Abu or a fluorinated derivative or formula II:

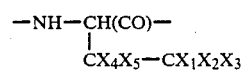

II wherein $X_1$ to $X_5$ independently are H or F with the proviso that at least one of $X_1$, $X_2$, $X_3$, $X_4$ and $X_5$ is F;

$R^3$ is Sar, D-MeAla or a fluorinated analog thereof;

$R^4$, $R^9$ and $R^{10}$ independently are MeLeu or a fluorinated analog thereof;

$R^5$ is Val or a fluorinated analog thereof;

$R^6$ is MeAla, MeAbu, or a fluorinated analog thereof;

$R^7$ is Ala or a fluorinated derivative thereof;

$R^8$ is (a) D-Ala or a fluorinated derivative thereof; or (b) O-acyl-D-Ser or O-acyl-D-Thr wherein the acyl group is defined as $R^{12}$—CO— where $R^{12}$ represents hydrogen, $C_{1-6}$alkyl, phenyl or substituted phenyl of the formula;

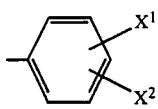

wherein $X^1$ and $X^2$ independently are
(a) $C_{1-6}$alkyl;
(b) $C_{1-6}$alkanoyl;
(c) $CH_2OH$;
(d) halo;
(e) $C_{1-6}$alkoxy;
(f) —$NH_2$;
(g) —$NO_2$;
(h) —COOH;
(i) —$COOC_{1-6}$alkyl; or
(j) —H; and $R^{11}$ is L-MeVal or a fluorinated derivative thereof.

2. A compound of claim 1 wherein
$R^1$ is MeBmt or dihydro MeBmt;
$R^2$ is Abu;
$R^3$ is Sar or D-MeAla;
$R^4, R^9$ and $R^{10}$ independently are MeLeu or a fluorinated analog thereof;
$R^5$ is Val or a fluorinated analog thereof;
$R^6$ is MeAla, MeAbu, or a fluorinated analog thereof;
$R^7$ is Ala;
$R^8$ is D-Ala; and
$R^{11}$ is MeVal or a fluorinated analog thereof.

3. A compound of claim 2 wherein
$R^1$ is MeBmt;
$R^2$ is Abu;
$R^3$ is Sar;
$R^4, R^9$ and $R^{10}$ are MeLeu;
$R^5$ is Val;
$R^6$ is MeAla;
$R^7$ is Ala;
$R^8$ is D-Ala; and
$R^{11}$ is MeVal.

* * * * *